US005281727A

United States Patent [19]
Carver et al.

[11] Patent Number: 5,281,727
[45] Date of Patent: Jan. 25, 1994

[54] METHOD OF USING ION EXCHANGE MEDIA TO INCREASE TAXANE YIELDS

[75] Inventors: David R. Carver; Timothy R. Prout; Christopher T. Workman; Donia L. Henderson; Charles L. Hughes, all of Boulder, Colo.

[73] Assignee: NaPro BioTherapeutics, Inc., Boulder, Colo.

[21] Appl. No.: 982,391

[22] Filed: Nov. 27, 1992

[51] Int. Cl.$^5$ ............................................ C07D 305/14
[52] U.S. Cl. ...................................... 549/510; 549/511
[58] Field of Search ................................. 549/510, 511

[56] References Cited

PUBLICATIONS

Senilh et al *Journal of Natural Products*, vol. 47, No. 1, p. 131 Jan.-Feb., 1984.
B. Saha et al, *Tetrahedron Letters*, No. 35, pp. 3095-3098 (1977).

*Primary Examiner*—Alan L. Rotman
*Assistant Examiner*—Ba K. Trinh
*Attorney, Agent, or Firm*—Timothy J. Martin; Dana S. Rewoldt

[57] ABSTRACT

The present invention is a method that uses an absorption column for the cleavage and recovery of taxanes, which are not normally detected as free taxanes. The method processes a first solution that contains standard detectable taxanes and other undetectable taxane compounds to generate a second solution that contains a higher percentage of detectable standard taxane then the first solution. The first step of this method is loading a column having a first opening and a second opening with an ion exchange media. The next step is placing the first solution in the first opening of the column so that the first solution passes through the ion exchange media in the column and flows to the second opening. Thus, the taxane compounds are converted   standard taxanes by an ion exchange reaction and the second solution is formed. Then the next step is collecting, from the second opening of the column, the second solution and recovering from the second solution a larger percentage of standard taxanes then was detectable in the first solution. The ion exchange media of the present solution is an ion exchange resin. The ion exchange resin can be a mixture of an anion exchange resin and a cation exchange resin. The anion exchange resin is in the OH- form. The cation exchange resin is in the H+ form. Preferably, the ion exchange resin is alumina.

17 Claims, No Drawings

METHOD OF USING ION EXCHANGE MEDIA TO INCREASE TAXANE YIELDS

FIELD OF THE INVENTION

The present invention relates to the recovery and cleavage of taxanes from extracts of natural vegetation. More specifically, the present invention is a method for isolating undetectable taxanes from an extract taxane material that contains detectable and undetectable taxanes. The method of the present invention, more particularly relates to the use of an adsorption column for the cleavage and recovery of bound taxanes which are normally not detected to free taxanes which are detectable.

BACKGROUND OF THE INVENTION

In test studies, taxol has been shown to possess antitumor activity in various cancerous tumors. Taxol is a natural product which, unfortunately, is found in only small concentrations in the *Taxus brevifolia* species such as the Pacific Yew tree. In view of the limited supply of taxanes and the large commercial demand for taxanes, chemists have expended significant energies in finding various methods to increase the yield of taxanes from extraction of the Yew trees. Specifically, taxol, Baccatin III, 10-deacetylbaccatin V, 7-epitaxol, 10-deacetylbaccatin III and cephalomannine, (the standard taxanes) and other members of the taxane family of diterpenes have attracted the interest of cancer researchers Taxol has the structure below:

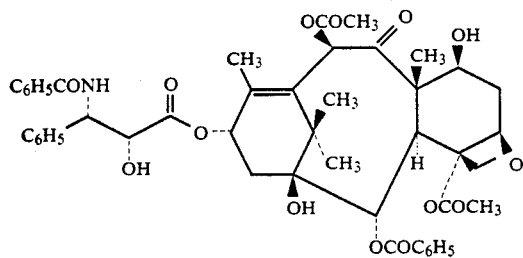

The above identified structure is recognized as taxol by high pressure liquid chromatography (HPLC). However, some compounds (which are not standard taxanes) that contain taxol or the taxol nucleus, i.e., the 20 carbon ring structure are not recognized as taxol by HPLC. These compounds may be unrecognized because the taxane nucleus may be bound to other large molecules so that the resultant molecule is not recognized as standard taxane by the standard tests. For example, sugar bound taxol is not readily recognized as a standard taxane by HPLC.

There has been some sugar bound taxols, such as 7-xylosyl taxol and 7-xylosyl-10-deacetyltaxol isolated and identified in the literature. See, V. Senilh et. al., *Journal of Natural Products*, 47, 131-137 (1984). It is highly possible that taxol which is insoluble is transported within the Yew tree in a bound form that is soluble. The addition of a sugar molecule to taxol would be expected to make the taxol significantly more soluble and thus more readily transported throughout the needles and twigs of the live Yew tree.

The same article mentioned above, indicates that an alumina adsorption column has been employed in the purification of an extract containing taxanes. In the paper written by Senilh et. al. *Journal of Natural Products*, Vol. 47, No. 1, pg. 131, January-February (1984), it appears that a relatively purified taxane sample was passed through an alumina column. This article reported that the miscelle, i.e. crude taxane sample, was extracted from Taxus brevifolia biomass by ethanol. Then the crude extract was subjected to evaporation and then subjected to a liquid/liquid partition using $H_2O/CH_2Cl_2$. Next, the aqueous phase of the separation was discarded and the organic phase of the separation was combined with various solvents. Thereafter, the taxane material, which was in the relatively purified state, was passed through a silica gel column and then an alumina column.

This paper does not appear to have reported an increase in the taxol recovered from the extract. The lack of a reported increase is most probably due to the fact that the aqueous phase of the liquid/liquid partition was discarded. Assuming that undetectable taxanes are water soluble, then these water soluble taxanes were probably discarded with the aqueous phase of the $H_2)/CH_2Cl_2$ liquid/liquid partition step. Thus, no increase in yield could be reported because the soluble taxanes such as sugar bound taxanes were discarded. There remains a need for a process that will isolate, purify and cleave taxanes that are present in an extract but are not readily detectable.

SUMMARY OF THE INVENTION

An object of the present invention is to isolate taxanes that are present in an unpurified taxane mixture.

Still another object of the present invention is to process taxanes in an extract such that a majority of these taxanes are converted to Baccatin III.

Yet a further object of the present invention is to increase the yield of taxanes in an extract above the expected baseline yield.

Another object of the present invention is to convert bound taxane material bound to free taxol or free Baccatin III or other free standard taxanes.

The present invention in its broadest form includes a method of processing a first solution that contains a percentage of detectable standard taxanes to generate a second solution containing a higher percentage of detectable standard taxanes than the first solution including the steps of: loading a column having a first opening and a second opening with an adsorbent packing media; placing the first solution in the first opening of the column so that the first solution passes through the packing media to the second opening thereby forming a second solution; collecting from the second opening of the column the second solution; and recovering from the second solution a larger percentage of standard taxanes than was detectable in the first solution.

These and other objects of the present invention will become more readily appreciated and understood from a consideration of the following detailed description of the preferred embodiment.

DETAILED DESCRIPTION OF THE PREFERRED EMBODIMENT

In its broadest form the present invention relates to the method of recovering taxane material from natural vegetation. More specifically, the present invention relates to a method of using ion exchange media to recover not only the detectable taxanes present in a first solution but also some taxanes that were not detectable.

In the preferred embodiment of the present invention, the first solution is a miscelle. The miscelle is generated by flowing a solvent such as methanol or ethanol through a biomass of bark or needles from the *Taxus brevifolia* species. The miscelle contain a large amount of solvent and a low concentration of taxane material. The amount of taxane contained in the miscelle or first solution is considered to be 100% of the taxane compounds available in the biomass.

Typically, the miscelle, which is analyzed to generate the baseline yield is either a bark extract or a needle extract. Both the bark of the Yew tree and the needles of a Yew tree contain taxane material. Either biomass, bark or needles, can be used with the present invention. However, the present invention shows markedly higher yields if a needle extract is used. It is hypothesized that needles require large quantities of sugar bound taxanes (i.e., water soluble taxanes) in order to transport the taxanes within the tree.

The first solution extracted from the biomass is analyzed for standard taxanes such as taxol, Baccatin III, 10-deacetyltaxol and 10-deacetylbaccatin III by high pressure liquid chromatography [HPLC] using either external or internal standards. The HPLC results are converted into a microgram per gram quantity of these taxanes in the original biomass. The micrograms of taxanes in this first solution is the baseline yield which is considered to be a 100% yield of the standard taxanes such as taxol, Baccatin III, 10-deacetyltaxol and 10-deacetylbaccatin III in the original biomass. Further processing of this first solution in accordance with the present invention results in unexpectedly high yields of these standard taxanes which often exceed the theoretical 100% yields.

The capability of the present invention to produce results that exceed the baseline yield of the first solution implies two things. One, there must be materials in the first solution that contain taxanes that were not detected as standard taxanes in the original miscelle extract. Two, the present invention must be producing taxol or Baccatin III or 10-deacetyltaxol or 10-deacetylbaccatin III from these undetected taxane materials. This undetectable taxane material is most likely derived from taxane compounds that contain a taxane nucleus but which are not readily recognized as a standard taxane due to other compounds which are bound to the nucleus. An example of this type of undetectable taxane material may be the 7-xylosyltaxol previously discussed.

Bound taxanes generally refer to molecules that contain the taxol nucleus, i.e., the 20 carbon member ring structure, but that have extra chemical structures such that the molecule does not analyze as a standard taxane. Free taxanes on the other hand are taxanes that are detectable by HPLC at the retention times established by external standards for taxanes such as taxol, 10-deacetylbaccatin III, Baccatin III, 10-deacetyltaxol etc.

Presently, the bound taxanes in the first solution, which through the use of the present invention result in free standard taxanes, have not been isolated. However, the method of converting the bound taxanes to free standard taxanes has been discovered.

The method of processing the first solution to convert bound taxanes into a second solution containing free taxanes employs an ion exchange media. Alumina and ion exchange resins, both types of ion exchange media, have been successfully employed to increase the taxane yield of miscelle extracts. First I will discuss the alumina column.

Alumina Column

In the process of attempting to purify extracts containing taxanes, a variety of alumina columns were employed. The taxane yield results were surprisingly varied. Some commercially available alumina showed low yields while others showed yields that surpassed the theoretical baseline yield of the taxanes. Gradually it became evident that higher yields resulted when the alumina was carefully produced to have the necessary basic character. Additionally, it was discovered that the temperature and the length of time that the first solution was contacted with the alumina could be adjusted to get the desired results.

Generally, if the first solution was passed through with the alumina column at room temperature (25°-27° C.) the contact time necessary to convert the bound taxol to free taxol was between 1-4 hours. However, if the temperature of the alumina gel was elevated to 30°-70° C. a shorter contact time, as little as 10-600 seconds was sufficient to give the increased yields of taxanes. The contact time is shortened by methods commonly used in the art. For example, a vacuum can be employed to quickly pull the fluid through the column or a high pressure flow of fluid can be employed to accelerate the rate at which the fluid passes through the column.

During the experimental process the temperature of the alumina was elevated to greater than 70° C. These temperatures showed surprisingly unexpected results. The second solution drawn from the column was analyzed and the results no longer indicated high yields of free taxol. Instead the heated alumina converted substantially all of the taxol to free Baccatin III and the 10-deacetyltaxol to free 10-deacetylbaccatin III. Surprisingly, there was only slight epimerization of the free Baccatin III. These taxane-yield increases were produced by an alumina material having an activity of one, initially.

When a second alumina which has an activity designated as "super one activity" was employed; this second alumina (commercially available) showed even more surprising results than the first alumina. The second solution after passing through the second alumina resulted in 449% yield of free Baccatin III at only 50° C. Later in the experimental process, it was discovered that adding external heat was not necessary to quickly convert the bound taxanes to free standard taxanes such as Baccatin III. If the alumina column is not conditioned prior to use, the contact of the first solution with the alumina results in an exothermic reaction. Although this exothermic reaction is not controlled, it effectively provides sufficient heat to convert the taxanes into a free taxol form.

Unexpected high yields of free taxol and free Baccatin III were also produced by passing the first solution through carefully prepared ion exchange resins. The yields of first solutions from bark extractions which were passed through the ion exchange resins were often 115% of the base yield and first solutions from needle extractions were often 150% of the base yield.

The mechanism by which the ion exchange resin converts bound taxol to free taxol is believed to be the same mechanism by which alumina converts the bound taxol to free taxol. The mechanism is probably a base catalyzed cleavage of the taxane nucleus from a large molecule. This mechanism probably acts to cleave sugar molecules from the 7th position of the taxane.

Xylose linkages are known to be difficult to cleave thus, the anion exchange resin is most likely the catalyst in this mechanism.

The most common type of resin used in ion exchange media for both anion and cation exchange resins are polystyrene polymers with crosslinking divinylbenzenes. A cation exchange resin is derivatized with sulfonic acid, and an anion exchange resin is derivatized with the quaternary ammonium group. The cation exchange resin and the anion exchange resin can be loaded with whatever anion and cation is desired. For example, a typical deionizing water purification system contains a mixed bed deionizing cartridge containing anions and cations preconditioned to exchange H+ and OH−.

It has been hypothesized that the anion exchange resin is the catalyst used in converting bound taxol to free taxol. This hypothesis is further supported by the fact that the use of an anion exchange resin by itself increases the yield of the free taxanes. However, to avoid the epimerization of the taxane material, a mixed bed of anions and cations preconditioned to exchange H+ and OH−, like the deionizing water purification, is preferred.

It was anticipated that the presence of the cation exchange (H+) could be eliminated if a anion exchanger weaker than the OH−, such as OAc− (acetate) was loaded on the anion resin. When the weaker anion resin was employed the OAc− (acetate) anion exchanger showed some increase in the yield of taxanes, however, these yields were not as impressive as the yields from a mixed bed of resins having a OH− and H+ exchange.

Since regeneration of the ion exchange material would be simplified if the cation and anion exchange resins were separate and not mixed, an experiment passing the first solution through the anion resin and cation resin separately was performed. The anion exchange resin (OAc−) and the cation exchange resin (H+) was loaded onto two separate columns and the extract was passed through each. Surprisingly, regardless of the order of passage of the extract, the large increases in taxane material shown by the mixed bed of resins was not observed. In fact, each pass of the solution through the separate materials after the first pass appeared to decrease the free taxanes.

Unless defined otherwise, all technical and scientific terms used herein have the same meaning as commonly understood by one of ordinary skill in the art to which this invention belongs. Methods and materials similar or equivalent to those described herein are considered within the scope of the present invention. The following non-limiting examples are provided.

EXAMPLE I

A 65 ml methanolic extract from the bark of Taxus brevifolia containing a 0.05 g/ml residue was the sample material (SAMPLE I). This sample had 6085 micrograms of taxol detected by HPLC. Baccatin III was not detected in the sample. This sample was passed through a heated column of alumina. The 15 mm×30 cm column, a jacketed West condenser was packed with 25 grams of alumina (commercially available). This alumina had activity 1. The lower the activity number, the more strongly the alumina binds. This alumina had a surface area of 150-200 square meter/gram, a mesh size of 50-200 microns and a pH range of 7.4-9.0. The alumina was heated to 55°-60° C. by a recirculation heat bath and then conditioned by passing 50 ml of pure methanol through the column. Conditioning is necessary to control the temperature because the solvent when placed in contact with dry absorbent media produces heat. After the alumina was conditioned, the sample was permitted to pass through the column over a period of 5 to 15 minutes. Thereafter the column was rinsed with 20 ml of methanol. The total combined solutions (Solution I) were collected and analyzed by HPLC.

|  | Sample I | Solution I |
|---|---|---|
| taxol | 6105 micrograms | 7363 micrograms |
| percentage of taxol | 100% | 121% |
| Baccatin III | 0 micrograms | 0 micrograms |
| percentage of Baccatin III | 0% | 0% |
| 10-deacetyl Baccatin III | 3908 micrograms | 3727 micrograms |
| percentage of 10-deacetyl Baccatin III | 100% | 95% |

The additional yield of free taxol beyond the baseline yield of taxol is presumed to be because the alumina cleaves molecules from the taxane nucleus to form free taxol in the second solution that is detectable by HPLC. The relatively low increase in free taxol is due to the biomass employed to form the sample extract. The bark of the Taxus species probably contains significantly lower amounts of bound taxol, especially sugar bound taxol than the needles of the Taxus species.

EXAMPLE II

Three methanolic extracts from the needles of Taxus brevifolia were the sample materials. The first sample was 65 ml and had 250 micrograms of taxol and 334 micrograms of Baccatin III (Sample 1). The second sample was 20 ml and had 144.2 micrograms of taxol and 25.5 micrograms of Baccatin III detected by HPLC (Sample 2). The third sample had 5.04 grams of taxol and 1.23 grams of Baccatin III detected by HPLC (Sample 3). The samples were passed through a column of alumina. The 15 mm×30 cm column was packed with 25 grams of alumina (commercially available).

| Reaction Condition | Sample 1 |
|---|---|
| temperature | 60-70° C. |
| contact time | 1 minute |
| vacuum pressure | 15-20 psi |

|  | Sample 1 | Solution 1 |
|---|---|---|
| taxol micrograms | 250 micrograms | 220 micrograms |
| taxol percentage | 100% | 88% |
| Baccatin III micrograms | 334.3 micrograms | 1501 micrograms |
| Baccatin III percentage | 100% | 449% |
| 10-deacetyl Baccatin III micrograms | 0 micrograms | 0 micrograms |
| 10-deacetyl Baccatin III percentage | 0% | 0% |

The alumina was heated by a recirculation heat bath and then conditioned by passing 50 ml of pure methanol through the column. After the alumina was conditioned the Sample 1 was permitted to pass through the column under vacuum pressure of 15-20 psi for a period of 1 minute. In the preferred embodiment, the short contact time is because pressurized sample (20-40 psi) is passed through the column. Thereafter, the column was rinsed with 20 ml of methanol. The total combined solutions (Solution 1) were analyzed by HPLC. The results show over 1000 micrograms of free Baccatin III which was undetectable in the original Sample 1.

| Reaction Condition | Sample 2 | |
|---|---|---|
| temperature | 25° C. | |
| contact time | 30 minutes | |
| | Sample 2 | Solution 2 |
| taxol micrograms | 144.2 micrograms | 225 micrograms |
| taxol percentage | 100% | 156% |
| Baccatin III micrograms | 27 micrograms | 46 micrograms |
| Baccatin III percentage | 100% | 170% |
| 10-deacetyl Baccatin III micrograms | 123 micrograms | 126 micrograms |
| 10-deacetyl Baccatin III percentage | 100% | 102% |

The alumina was maintained at room temperature and conditioned by passing 20 ml of pure methanol through the column. After the alumina was conditioned, Sample 2 was passed through the column. Thereafter, the column was rinsed with 20 ml of methanol at room temperature. The total combined solutions (Solution 2) were analyzed by HPLC. The HPLC results indicated 8 additional micrograms of free taxol and 21 additional micrograms of free Baccatin III.

| Reaction Condition | Sample 3 | |
|---|---|---|
| temperature | 25° C. | |
| contact time | 1-2 hours | |
| | Sample 3 | Solution 3 |
| taxol grams | 1.23 grams | 5.04 grams |
| taxol percentage | 100% | 410% |
| Baccatin III grams | 0 grams | 0 grams |
| Baccatin III percentage | 0% | 0% |
| 10-deacetyl Baccatin III | 0 grams | 0 grams |
| 10-deacetyl Baccatin III percentage | 0% | 0% |

The alumina column was not heated, however, this experiment was performed without any conditioning. Therefore, this experiment was run in uncontrolled heat. When Sample 3 hit the alumina there was an exothermic reaction. This uncontrolled heat resulted in a surprising yield of free taxol. It appears that the heat was not sufficient to cleave the taxol side chain from the taxane nucleus but was sufficient to cleave the large bound molecules from the taxol nucleus. The HPLC analyze of the rinse solution and the drawn off solution (Solution 3) indicated almost 4 additional grams of free taxol.

EXAMPLE III

A single sample, methanolic extract from the needles of Taxus brevifolia was the sample material. This sample was passed through a heated column of alumina. The 15 mm × 30 cm column had a cotton plug to retain the 25 grams of alumina (commercially available) packed within the column. This alumina was heated by a recirculation heat bath to 50° C. and then conditioned by passing 50 ml of a solution of 10% $H_2O$ and 90% methanol through the column. After the alumina was conditioned the sample was permitted to pass through the column over a short period of time, approximately 10-600 seconds. Thereafter, the column was rinsed with 20 ml of methanol. The total combined solutions were analyzed by HPLC and the result was a 400% increase of Baccatin III over the 100% baseline yield of the original first solution. It appeared that all of the free taxol was converted to Baccatin III. This is a method by which crude taxane extracts containing taxol and presumably other taxanes could be converted to Baccatin III.

EXAMPLE IV

An anion exchange resin, commercially available under the name Dowex-1X8, was treated to be in the $OH^-$ form. The anion exchange resin was converted into the OH- form by passing 200 ml of 2M sodium hydroxide through the resin. The residual basic solution was then rinsed off of the resin by passing deionized water through the resin until the pH of the filtrate was below 8.

A cation exchange resin, commercially available under the name Dowex-50X8, was treated to be in the $H^+$ form. The cation exchange resin was converted into the $H^+$ form by passing a large quantity of hydrochloric acid 1M-3M through the resin. The residual acidic solution was then rinsed off of the resin by passing deionized $H_2O$ through the resin until the pH of the filtrate was above 6.

Next, 2 grams of the Dowex-50X8 ($H^+$) was mixed with 2 grams of the Dowex-1X8 ($OH^-$) to form a homogeneous bed of mixed resin. A 25 ml methanolic extract from Taxus brevifolia bark containing 433 mg of free taxol by HPLC analysis (Solution IV) was allowed to percolate for 5 minutes through the mixed bed of resins at room temperature. The resin was then rinsed with 25 ml of pure methanol and the resultant combined solutions were analyzed by HPLC (Solution IV).

| | Sample IV | Solution IV |
|---|---|---|
| taxol micrograms | 357 micrograms | 443 micrograms |
| taxol percentage | 100% | 124% |
| Baccatin III micrograms | 463.96 micrograms | 1545 micrograms |
| Baccatin III percentage | 100% | 333% |

The increase yields of free Baccatin III and free taxol shown by the ion exchange resins are similar to the increase yields that resulted from using the alumina column.

EXAMPLE V

An anion exchange resin, commercially available under the name Dowex-1X8, was treated to be in the $OAc^-$ (acetate) form. The anion exchange resin was converted first into the $OH^-$ form by passing 200 ml of 2M sodium hydroxide through the resin. The residual basic solution was then rinsed off of the resin by passing deionized water through the resin until the pH of the filtrate was below 8. This anion exchange resin was converted to the $OAc^-$ form by passing a dilute (0.5 to 2M) solution of acetic acid through the resin and the acid residue was rinsed off by deionized $H_2O$.

A cation exchange resin, commercially available under the name Dowex-50X8, was treated to be in the H+ form. The cation exchange resin was converted into the H+ form by passing a large quantity of hydrochloric acid 1M-3m through the resin. The residual acidic solution was then rinsed off of the resin by passing deionized H$_2$O through the resin until the pH of the filtrate is above 6.

4 grams of the Dowex-50X8 (H+) and 4 grams of the Dowex-1X8 (OAc−) were used to form two separate beds of resin. A 76 ml methanolic extract of Taxus brevifolia bark containing 2149 micrograms of free taxol, 218 micrograms of free Baccatin III and 1200 micrograms of free 10-deacetylbaccatin III by HPLC analysis (Sample V) was allowed to percolate through the anion bed of resin at room temperature. The percolate time was approximately 5 minutes. The resin was then rinsed with 25 ml of pure methanol and the resultant combined solutions were analyzed by HPLC. The results are shown as solution $V_1$. Next the solution $V_1$ was passed through the cation bed of resins at room temperature and rinsed with 25 ml of pure methanol and the resultant combined solution (Solution $V_2$) were analyzed by HPLC. Solution $V_2$ was then repassed through the anion bed and then again through the cation bed. The initial pass through the anion bed resulted in an increase in the free Baccatins. However, the results showed consistent decreases in the free taxol, free Baccatin III and free 10-deacetylbaccatin III with each pass through either column after the first pass through the anion bed.

|  | Sample V | Solution $V_1$ | Solution $V_2$ |
| --- | --- | --- | --- |
| taxol micrograms | 2149 micrograms | 2120 micrograms | 1787 micrograms |
| taxol percentage | 100% | 98.6% | 83% |
| Baccatin III micrograms | 218 micrograms | 330 micrograms | 284 micrograms |
| Baccatin III percentage | 100% | 150% | 130% |
| 10-deacetyl Baccatin III micrograms | 1200 micrograms | 1223 micrograms | 951 micrograms |
| 10-deacetyl Baccatin III percentage | 100% | 120% | 79% |

The anion OAc− exchange resin does show some increase in free taxanes in the first pass. The free Baccatin III and 10-deacetyl Baccatin III taxol begin to decrease when passed through the the cation H+ exchanger. The increases in yields from the first pass through the anion bed was substantially less than shown in the mixed bed of resins or the alumina experiments.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A method of processing a first solution that contains detectable standard taxanes and other taxane compounds to generate a second solution containing a higher percentage of detectable standard taxanes than said first solution including the steps of:

loading a column having a first opening and a second opening with an ion exchange media;

placing said first solution in said first opening of said column so that said first solution passes through said ion exchange media to said opening thereby said taxane compounds are converted to standard taxanes by an ion exchange reaction wherein a second solution is formed;

collecting from said second opening of said column said second solution; and recovering from said second solution a larger percentage of standard taxanes than was detectable in said first solution.

2. A method according to claim 1 wherein said ion exchange media is ion exchange resin.

3. A method according to claim 2 wherein said ion exchange resin is a mixture of anion exchange resin and cation exchange resin.

4. A method according to claim 3 wherein said anion exchange resin is in the OH− form.

5. A method according to claim 4 wherein said cation exchange resin is in the H+ form.

6. A method according to claim 1 wherein said ion exchange media is alumina.

7. A method according to claim 6 wherein said alumina is heated to greater than 50° C. whereby the second solution contains taxanes primarily in the form of Baccatin III.

8. A method according to claim 1 wherein said ion exchange media is at 25° C.

9. A method according to claim 1 wherein said first solution contains said detectable standard taxanes, other taxane compounds, residue and solvent.

10. A method according to claim 9 wherein said solvent is an alcohol.

11. A method according to claim 1 wherein said standard taxanes in said second solution are in the form of taxol.

12. A method according to claim 1 wherein said standard taxanes in said second solution are in the form of Baccatin III.

13. A method of processing an extract that contains a baseline amount of free standard taxanes and some amount of bound taxanes to generate a second solution that contains an amount of free standard taxanes that exceed the baseline amount including the steps of:

providing an ion exchange media adapted to be packed into a column;

packing said media in said column;

contacting said extract with said media within said column such that said extract passes down said column and said bound taxanes are converted into said free standard taxanes; and collecting a second solution from said column that contains an amount of free standard taxanes that exceeds the baseline amount of taxanes in the extract.

14. A method according to claim 13 wherein said baseline amount of standard taxanes is a 100% yield and said amount of free standard taxanes in the second solution exceeds 115% yield of taxanes.

15. A method according to claim 13 wherein said media is an ion exchange resin.

16. A method according to claim 13 wherein said media is an alumina gel.

17. A method according to claim 13 wherein said ion exchange media is elevated to a temperature above 125° C. and said free standard taxanes in said second solution are in the form of Baccatin III.

* * * * *